United States Patent
Piljac et al.

(10) Patent No.: US 7,262,171 B1
(45) Date of Patent: Aug. 28, 2007

(54) USE OF RHAMNOLIPIDS IN WOUND HEALING, TREATING BURN SHOCK, ATHEROSCLEROSIS, ORGAN TRANSPLANTS, DEPRESSION, SCHIZOPHRENIA AND COSMETICS

(75) Inventors: Tatjana Piljac, Zagreb (HR); Goran Piljac, Davis, CA (US)

(73) Assignee: Paradigm Biomedical, Inc.

( * ) Notice: Subject to any disclaimer, the term of this patent is extended or adjusted under 35 U.S.C. 154(b) by 1045 days.

(21) Appl. No.: 09/644,984

(22) Filed: Aug. 24, 2000

Related U.S. Application Data

(60) Division of application No. 09/644,984, filed on Aug. 24, 2000, and a continuation of application No. PCT/US99/03714, filed on Feb. 24, 1999.

(60) Provisional application No. 60/075,959, filed on Feb. 24, 1998.

(51) Int. Cl.
*A61K 31/7028* (2006.01)

(52) U.S. Cl. ............................................. 514/25
(58) Field of Classification Search ................... 514/25
See application file for complete search history.

(56) References Cited

U.S. PATENT DOCUMENTS 5,466,675 A * 11/1995 Piljac et al. .................. 514/25
5,547,988 A *  8/1996 Yu et al. ..................... 514/557

* cited by examiner

*Primary Examiner*—Leigh C. Maier
(74) *Attorney, Agent, or Firm*—Evelyn A. Defilló; Defillo & Associates, Inc.

(57) ABSTRACT

Various methods are provided, including wound healing with reduced fibrosis, treatment of burn shock, treatment and prevention of atherosclerosis, prevention and treatment of organ transplant rejection, treatment of depression and schizophrenia and treatment of the signs of aging, such as wrinkles, each of which uses administration of a composition containing one or more rhamnolipids as an active ingredient.

7 Claims, 3 Drawing Sheets

USE OF RHAMNOLIPIDS IN WOUND HEALING, TREATING BURN SHOCK, ATHEROSCLEROSIS, ORGAN TRANSPLANTS, DEPRESSION, SCHIZOPHRENIA AND COSMETICS

CROSS REFERENCE TO RELATED APPLICATION

This application is Divisional of Ser. No. 09/644,984 filed Aug. 24, 2000, entitled "USE OF RHAMNOLIPIDS IN WOUND HEALING, TREATING BURN SHOCK, AND COSMETICS".

This application is a continuation of International Application No. PCT/US99/03714 filed Feb. 24, 1999, which was filed as U.S. Ser. No. 60/075,959, filed Feb. 24, 1998.

The work described herein was financed in part by NIH grant SBIR 96-2 No. IR43AR44443-01 ZRG3 SSS-Z(6).

BACKGROUND OF THE INVENTION

1. Field of the Invention

The present invention relates to the use of rhamnolipids in re-epithelization of skin, particularly in wound healing with the diminution of fibrosis. The present invention also relates to the use of rhamnolipids in the prevention and treatment of burn shock, treatment and prevention of atherosclerosis (cardiovascular diseases), prevention and treatment of rejection of transplanted organ and in the treatment of depression and schizophrenia. The present invention further relates to the use of such rhamnolipids in cosmetic preparations.

2. Discussion of the Background

Typically, when an adult human receives an injury, either through burning of tissue or an incision in the skin tissue, the wound heals to leave a scar. This is even true in the case of post-surgical recovery where the wound has been closed with sutures (although scarring is generally less in such cases). This is not the case, however for wounds to fetuses. It is known that wounds in fetuses heal rapidly and generally without scar formation until late in gestation. Reasons for this include:

1. The dermis is the location of the scar in adult wounds. As development progresses, dermal collagen is deposited and sulfated glycosaminoglycans (GAG) replace non-sulfated GAG of which hyaluronic acid (HA) is predominant.

2. Fetal tissue appears to be intrinsic in repair with reduction of fibrosis, and the major fetal cell type responsible for such repair may be the fetal fibroblast.

3. The fetal immune system is functionally immature relative to the adult immune system and plays a much less prominent role in fetal wound healing.

4. The fetal extracellular matrix (ECM) differs from that in adults in having HA, collagen, elastin, and adhesion glycoproteins as the major components.

It has been shown that hyaluronic acid levels in both fetal and adult sheep wounds rapidly increase until three days after wounding. This elevated level persists at least 21 days after wounding in the fetus, whereas it rapidly returns to baseline in the adult. In adult wounds, HA is deposited briefly within a fibrin and platelet plug. The HA is removed by hyaluronidase, and this provisional matrix is replaced by collagen and sulfated glycosaminoglycans. The deposition of collagen in fetal wounds is in a highly organized pattern that is indistinguishable from unwounded fetal dermis. Some of the major differences between fetal and adult repair are the temporal patterns of adhesion glycoproteins present in the wound, which are seen at the earliest stage of repair. These differences may lead to differences in cell mobility, migration, adhesion and proliferation.

Cytokines. Transforming growth factor-beta (TGF-beta) induces fibroplasia and increases wound tensile strength in adult wounds, and similar effects have been recorded in fetal wounds. In adults, activated macrophage products, such as cytokines and growth factors, progressively modify the local tissue environment, initially leading to destruction of tissue and later, i.e., in chronic delayed type hypersensitivity (DTH) reactions, causing replacement by connective tissue. The effects of macrophage-derived cytokines and growth factors occur in two phases. TNF, IL-1, and macrophage-derived chemokines acutely augment inflammatory reactions initiated by T-cells. These same cytokines also chronically stimulate fibroblast proliferation and collagen production. These slow actions of cytokines are augmented by the actions of macrophage-derived polypeptide growth factors. Platelet-derived growth factor, produced by activated macrophages, is a potent stimulator of fibroblast proliferation, whereas macrophage-derived growth factor (TGF-beta) augments collagen synthesis. Macrophage secretion of fibroblast growth factor causes endothelial cell migration and proliferation, leading to new blood vessel formation. The consequence of these slow actions of cytokines and growth factors is that prolonged activation of macrophages in a tissue, e.g., in the setting of chronic antigenic stimulation, leads to replacement of differentiated tissues by fibrous tissue. Fibrosis is the outcome of chronic DTH, when elimination of antigen and rapid resolution are unsuccessful.

There is thus a need to develop methods for inducing re-epithelization in adult skin tissue, to provide wound healing with reduction of fibrosis in adults, thereby reducing one of the detrimental effects of surgery and wound healing in general.

SUMMARY OF THE INVENTION

Accordingly, one object of the present invention is to provide a method for re-epithelization of skin for providing wound healing with reduced fibrosis using rhamnolipids as the active agent.

A further object of the present invention is to provide a method for treatment of burn shock using the rhamnolipids as the active agent.

Another object of the present invention is to provide a method for the treatment and prevention of atherosclerosis using rhamnolipids as the active agent.

Another object of the present invention is to provide a method for the prevention and treatment of the rejection of transplanted organs using rhamnolipids as the active agent.

Another object of the present invention is to provide a method for treatment of certain mental disorders, such as depression and schizophrenia, using rhamnolipids as the active agent.

Another object of the present invention is to provide a cosmetic composition useful for the treatment of the signs of aging, such as wrinkles.

These and other objects of the present invention have been satisfied by the discovery that rhamnolipids can provide the above noted treatments, particularly wound healing with reduced fibrosis and treatment of burn shock.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1 provides a graphical representation of the effects of topical BAC-3 on the rate of burn wound closure.

DETAILED DESCRIPTION OF THE PREFERRED EMBODIMENTS

Figure 1:
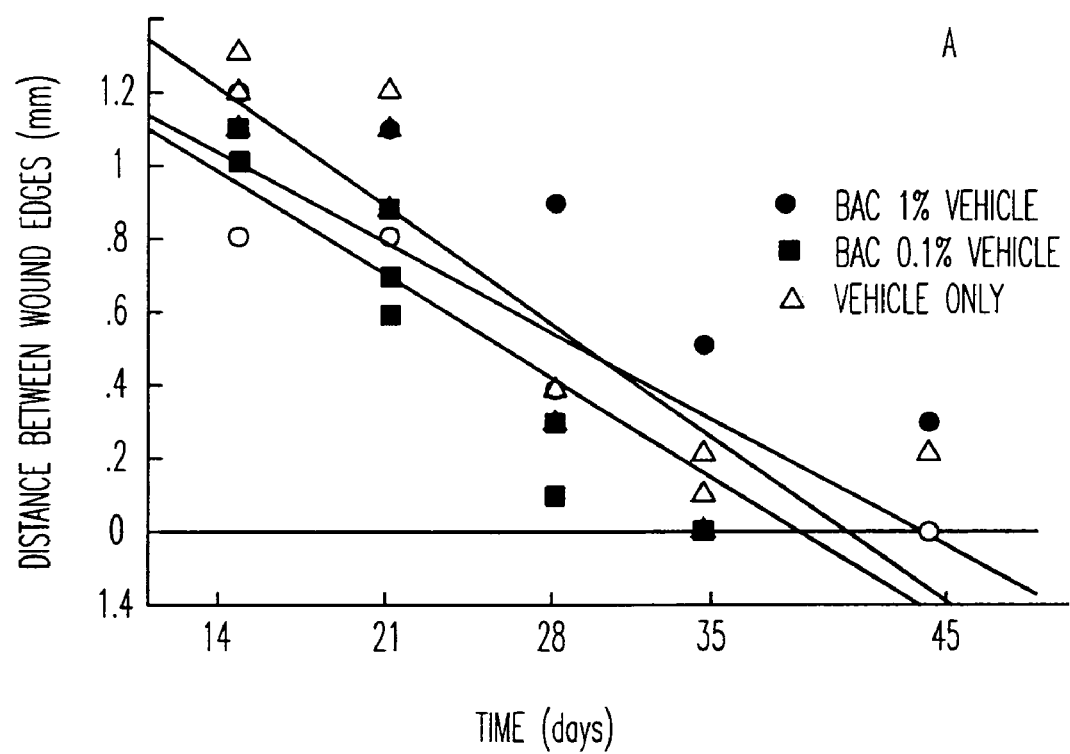

The present invention relates to pharmaceutical and/or cosmetic preparations and compositions comprising as the active ingredient, one or more rhamnolipids of Formula 1:

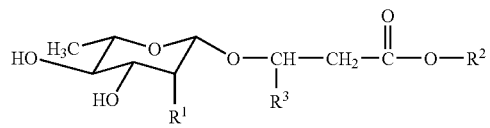

wherein $R^1$=H, α-L-rhamnopyranosyl (either unsubstituted or substituted at the 2 position with a group of formula —O—C(=O)—CH=CH—$R^5$), or —O—C(=O)—CH=CH—$R^5$;

$R^2$=H, lower alkyl (i.e. C1-C6 linear or branched alkyl, preferably —$CH_3$), —$CHR^4$—$CH_2$—COOH or —$CHR^4$—$CH_2$—$COOR^6$;

$R^3$=—$(CH_2)_x$—$CH_3$, wherein x=4-19;
$R^4$=—$(CH_2)_y$—$CH_3$, wherein y=1-19;
$R^5$=—$(CH_2)_z$—$CH_3$, wherein z=1-12; and
$R^6$=lower alkyl, preferably —$CH_3$.

The rhamnolipids of the present invention can be prepared by conventional methods, preferably by fermentation, isolation and purification as described in U.S. Pat. Nos. 5,455,232; 5,466,675 and 5,514,661, as well as BE 1005704A4, CA 2,129,542, JP 5-512946 and EP 93914523.1, each of which is hereby incorporated by reference.

In the methods of the present invention, the rhamnolipid that is preferred has the structure of formula:

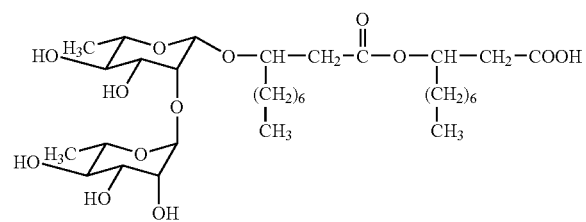

(α-L-rhamnopyranosyl-(1,2)-α-L-rhamnopyranosyl)-3-hyroxydecanoyl-3-hydroxydecanoic acid; hereafter referred to as "BAC-3")

Other preferred rhamnolipids include those wherein:

a) $R^1$=—O—C(=O)—CH=CH—$R^5$; $R^2$=—$CHR^4$—$CH_2$—COOH; $R^3$=—$(CH_2)_6$—$CH_3$; $R^4$=—$(CH_2)_2$—$CH_3$; and $R^5$=—$(CH_2)_6$—$CH_3$; or b) $R^1$=α-L-rhamnopyranosyl substituted at the 2-position by —O—C(=O)—CH=CH—$R^5$; $R^2$=—$CHR^4$—$CH_2$—COOH; $R^3$=—$(CH_2)_6$—$CH_3$; $R^4$=—$(CH_2)_6$—$CH_3$; and $R^5$=—$(CH_2)_6$—$CH_3$; or c) $R^1$=—O—C(=O)—CH=CH—$R^5$; $R^2$=—$CHR^4$—$CH_2$—$COOCH_3$; $R^3$=—$(CH_2)_6$—$CH_3$; $R^4$=—$(CH_2)_2$—$CH_3$; and $R^5$=—$(CH_2)_6$—$CH_3$; or d) $R^1$=α-L-rhamnopyranosyl substituted at the 2-position by —O—C(=O)—CH=CH—$R^5$; $R^2$=—$CHR^4$—$CH_2$—$COOCH_3$; $R^3$=—$(CH_2)_6$—$CH_3$; $R^4$=—$(CH_2)_6$—$CH_3$; and $R^5$=—$(CH_2)_6$—$CH_3$.

The structures of a)-d) are shown below:

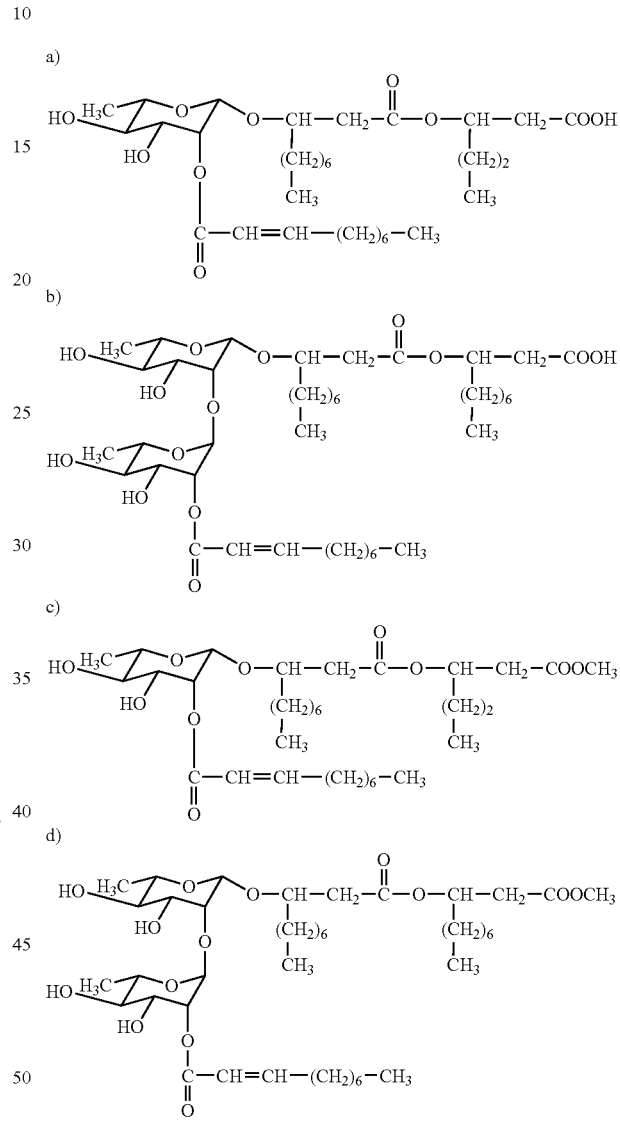

The toxicity and efficacy of these compounds can be further modified by varying the R groups as needed.

It has now been found that these rhamnolipids are effective in re-epithelization of the skin. This is important as it provides a method for wound healing with reduced fibrosis in non-fetal tissue.

Wound healing with diminished fibrosis is a main characteristic of fetuses. As noted above, responsible factors in fetuses are: 1. Fetal dermis; 2. Fetal tissue; 3. The fetal immune system; and 4. The fetal extracellular matrix (ECM). Accordingly, one method to achieve wound healing with reduced fibrosis in adults would be to change adult dermis, adult tissue, and adult ECM into fetal dermis, fetal tissue and fetal ECM. Unfortunately, this is not possible at this time. The present inventors reasoned that adult tissue could be enabled with the ability to heal without scars by blocking the factors responsible for scar healing without affecting the repair of wounds.

The method for wound healing with reduced fibrosis according to the present invention comprises applying to the wound, and optionally the surrounding area, an effective amount of a composition comprising one or more rhamnolipids of the present invention. Preferably, the rhamnolipid used in the method is the BAC-3 rhamnolipid described above. The composition comprising the rhamnolipid can be in the form of neat liquid, suspension, dispersion, emulsion, cream, tincture, powder, ointment or lotion. Preferably, the composition is in an ointment. The amount of rhamnolipid used in the treatment is 0.001% in the ointment up to 5% in the ointment, preferably from 0.01 to 1% in ointment, more preferably from 0.05 to 0.5% in ointment. (Unless otherwise indicated, all percentages are % by weight, based on total weight of the composition.) The ointment is applied directly to the subject area 1-5 times daily, preferably 2-3 times daily for a period of 1 day to 6 weeks, or until healing is complete.

Similarly, the present rhamnolipids can be used to treat burn shock. The same rhamnolipids useful for wound healing also appear to have an effect on cytokine production. It is believed that the main responsibility for wound healing lies in production of cytokines which are also responsible for shock, following large burns. These rhamnolipids are believed to prevent or reduce cytokine production. This reduction or prevention of cytokine production would have a beneficial impact in burn shock prevention. The treatment method can be either I.V./I.P. or orally. In such treatments the amount to be administered is from 1 µg/kg body weight of the patient to 50 µg/kg of body weight, preferably from 10 µg/kg to 30 µg/kg, from 1 to 4 times daily, preferably from 2 to 3 times daily, and for a period of from 1 day to 6 weeks. When used orally, the composition comprising the rhamnolipid(s) can be in any conventional orally administrable form, including but not limited to, solutions, tablets, capsules, emulsions, dispersions, and troches. When I.V. or I.P. administration is used, the composition comprising the rhamnolipid(s) can be in any conventional I.V. or I.P. administrable form, including, but not limited to, solution, neat liquid, dispersion, etc.

The same methods of administration used for burn shock can also be used in the treatment and/or prevention of organ rejection, depression, schizophrenia and atherosclerosis, using similar effective dosages.

A further use for the rhamnolipid containing composition of the present invention is in the preparation of a cosmetic composition comprising one or more of the rhamnolipids in an amount effective to treat signs of aging, such as wrinkles. Such a cosmetic composition would be applied from 1 to 3 times per day to the affected area. The cosmetic composition could be in any of the topical forms noted above and contain similar amounts of rhamnolipid(s).

The composition comprising the one or more rhamnolipids can further include, if desired, one or more carriers and/or diluents conventionally used in the pharmaceutical and/or cosmetic industries.

EXAMPLES

Having generally described this invention, a further understanding can be obtained by reference to certain specific examples which are provided herein for purposes of illustration only and are not intended to be limiting unless otherwise specified.

Open Wound Healing

The BAC-3 rhamnolipid was tested in the case of open wound healing, in a patient suffering around ten years from incurable venous ulcer. On the left leg, the patient had very thick layers of collagen with fibrotic lesions. After administration of 1% BAC-3 in the form of an ointment, twice daily during 41 days, the patient's condition was significantly improved. Moreover, after treatment was finished, not only the collagen, but also the fibrotic lesions had disappeared as well. One year after the treatment, the treated skin lesions on the left leg appear normal, and all skin collagen and fibrotic layers had disappeared.

Topical Administration of Rhamnolipids in Incision and Burn Wounds (Rats)

The wounding of animals was performed according to the Protocol for Animal Use and Care at the University of California-Davis (hereafter UC-Davis). The entire animal protocol required 70 Sprague-Dawley rats: 30 rats for incision wounds and 40 rats for burn wounds. Among them 36 rats were burned over 7% of their skin and 4 rats were burned over 15% of their skin. Incision wounds of whole skin and burn wounds were treated topically with 2 test doses of the pharmaceutical preparation of di-rhamnolipid BAC-3. Each dose contained a). 1%, and 0.1% of active di-rhamnolipid (BAC-3) in eucerin (eucerin=71.5 g Vaselinum album (Producer: D.E.A. Hamburg); 23.8 g Lanolinum (Producer I.O.I. Hamburg); 4.7 g Cholesterin (Producer: Solvay, Wiena, Austria); Water Number: 320); or b). 1%; 0.1% active rhamnolipid (BAC-3) with antiseptic (chlorhexidine hydrochloride-PLIVA-Zagreb). Eucerin with BAC-3 was administrated twice daily during healing. The same experiment had one control group without treatment, and one control group which was treated with ointment+1% chlorhexidine hydrochloride. During the experiment, animal body weight and behavior was checked every third day, and photographs were taken periodically.

Burn wounds. The consecutive burn wounds should ideally be identical in depth and extent. The standard method defines the size and location of the burn wound, the temperature gradient, duration of exposure and method of applying the burn.

The wound surface areas tested were of two different sizes. One size to 7% of the body surface, which enables one to compare rate of wound healing with different percentage of BAC-3 and the other size to 15% of the body surface, which is a sufficient size so that healing could not occur by contraction alone. On the other hand, the total wound surface area should not cause major systematic problems. The latter can be concluded from undisturbed weight gain of the animals. The standard animal burn was performed by techniques and device described by Walker. The burning devices were prepared using a model device ordered from U.S. Army Surgical Research Unit, Experimental Surgery, Army Medical Center, Fort Sam Houston, Tex. 78234. The devices had apertures which enabled exposure of 7% and 15% of the total rat skin surface. The surface of the skin was measured for every animal using Mech's formula: $A=kW^{2/3}$; $A$=surface area in $cm^2$; $W$=body weight in grams; $k$=10.

Method of burning. Each animal was anesthetized with sodium pentobarbital administered i/p (5 mg/25 g). (Producer: Veterinary Laboratory Inc. Lenexa, Kans.). The hair over the dorsum was clipped with animal clippers. The animal was placed supine in the burning device and the extremities were tied; the malleable retractor was placed over the animal and secured snugly with plastic straps. The entire device was then picked up by the retractor ends with forceps and the exposed area was immersed in boiling water. Ten seconds of exposure was sufficient to produce a full-thickness burn. On removal from the water, the dorsum was quickly dried by rolling on a towel and the animal was released and individually caged. This procedure produces a uniform burn with sharp margins.

In this way the severity of the burn was such that sufficient observation time was achieved, while total healing occurred and classification of wound healing characteristics with respect to different topical agents was feasible.

On post burn days 7, 14 and 45, animals were sacrificed by overdose of sodium pentobarbital and skin specimens were taken for histopathology. Specimens included the wound bed as well as the healthy skin of the wound margins.

The specimens were fixed, and two stainings were routinely performed: Hematoxylin-Eosin (H&E) for microscopic evaluation, Verhoeff's staining for a better visualization of the crust and the regenerating dermis, and the alpha smooth muscle acting to identify the myofibroblasts. Microscopic findings were interpreted by a veterinarian pathologist.

During the microscopic and macroscopic observations, four wound healing parameters were evaluated: crust formation, re-epithelialization, formation of granulation tissue and inflammation.

Incision wounds. Dorsal midline incisions were made in anesthetized rats. The animals were clipped free of their fur and prepared with alcohol. A 5.0 cm, midline, full-thickness incision was made with a scalpel through the panniclus carnosus.

The wounds were immediately closed with skin sutures spaced at a distance of 0.5 cm. Seven days later, all sutures were removed. On days 14 and 21 after incision, three animals from each group were killed using an overdose of sodium pentobarbital. Using a plexiglass template, a minimum of two samples of full-thickness skin were harvested perpendicular to the long axis of the wound for tensile strength determination. The skin samples were 9.0 mm wide at the wound by 2.0 cm long.

Tensile Strength Determination. The standard wound samples for each treatment cohort were examined for tensile strength by pulling the individual wounds apart in an Instron 4201 (Universal Testing instruments, Instron Engineering Co., Canton, Mass.) material tester. Special clamps were used to securely grip the tissue to avoid slippage as the wounds were pulled at a standard cross speed of 25 mm/min. The tensile strength of healthy skin was measured in killed animals from each group.

Vertebrate Animals

Subjects used were male Sprague-Dawley rats 5 to 6 weeks old. Rats were housed in polypropylene cages with mere mesh lids and solid floors containing 1 cm depth of wood shavings. Animals were housed and placed in an air conditioned room at 21° C. (+/−2)C.°, 52-73% relative humidity, 15 fresh air changes per hr and 12 hr light/dark cycle. Animals were fed with a synthetic pellet diet, freshly obtained and not preserved with pesticides, containing all essential nutrients and stored under standard conditions and water ad libitum.

Animals were acclimatized for at least one week before the start of the study and were 7 weeks old at the time of treatment. They were allocated to the various experimental groups using a system of random numbers, and group body weights were checked on the day of treatment to ensure they did not differ from the overall mean by more than 5%.

Animals were caged individually.

Veterinary Care of Animals

All work (animal housing, experimentation, euthanasia, disposal) was performed substantially in accordance with the International Guiding Principles for Biochemical Research Involving Animals as stipulated by the Council for International Organizations of Medical Science using the Protocol of UC-Davis, Version of 1119/95.

Results

Burn Wounds.

A). Burning 7% Body Surface. (7×3 cm)

36 rats were divided into 6 groups. Each group had six animals. After burning rats according to the above-described procedure, each rat was caged individually. Before caging, the burned skin was smeared with the following different kinds of ointment:

1. 1 A-Six rats were smeared twice daily with 1% of BAC-3 in ointment.

2. 1 B-Six rats were smeared twice daily tenth 0.1% of BAC-3 in ointment 3. 1 D-Six rats were smeared twice daily with ointment only 4. 2 A-Six rats were smeared twice daily with 1% of BAC-3 in ointment plus 1% chlorhexidine hydrochloride 5. 2 B-Six rats were smeared twice daily with 0.1% BAC-3 in ointment plus 1% chlorhexidine hydrochloride 6. 2 D-Six rats were smeared twice daily with ointment only plus chlorhexidine hydrochloride.

From each group on days 7, 14 and 21 one rat was sacrificed for histopathological examination.

On day 45 the rest of three rats from each group were sacrificed. Sacrifice of the rats were done according to the described procedure using an overdose of sodium pentobarbital.

During 45 days all animals were evaluated for the following healing parameters: crust formation, inflammation, formation of granulation tissue and re-epithelization.

There were no significant differences in crust formation between groups. But inflammation during wound healing was mostly pronounced in the group 1-D and 2-D. (Placebo groups with or without chlorhexidine hydrochloride).

Granulation tissue was prominently developed in the groups 1-A and 2-A.

Re-epithelization in the middle part of the burn wounds was faster on all rats of the groups 1-B and 2-B. Unfortunately chlorhexidine hydrochloride in combination with BAC-3 irritated wounds and rats treated by 1% chlorhexidine always scratched the lower part and upper part of the burn wounds. Therefore, only the collagen area of all rats treated without 1% chlorhexidine was calculated.

Histopathologic Data on Rats Sacrificed on $45^{th}$ Day without Chlorhexidine Hydrochloride Using NIH Protocol.

Mean value of collagen tissue expressed in $mm^2$.

Group 1 A=8.48 $mm^2$

Group 1 B=5.15 $mm^2$

Group 1 D=6.46 $mm^2$

If we take the mean value of collagen concentration in the group 1 D (placebo) as a 1100%, then group 1 B (0.1% of BAC-3) had a mean value of collagen concentration of 79.72 and the group 1 A (1% of BAC-3) had a mean value of collagen concentration of 131.26.

Figure 2:
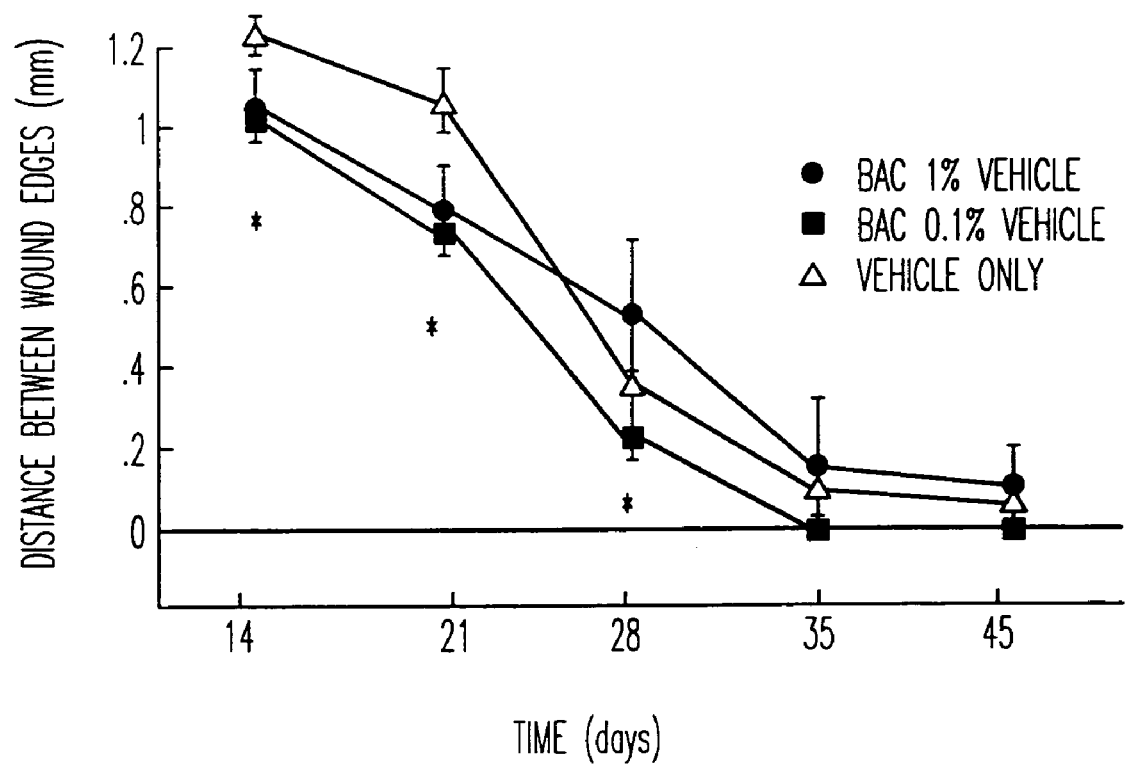
FIG. 2 provides a graphical representation of the effects of topical BAC-3 on the extent of burn wound closure.

The effects of topical BAC-3 on the rate of burn wound closure without chlorhexidine is shown on FIG. 1 and on the extent of burn wound closure is shown on FIG. 2.

Rate of burn wound closure with BA C-3 without chlorhexidine hydrochloride (FIG. 1). Burns were induced on the dorsal surface of rats using standardized methods as described previously. The total burn area was equivalent to 7% of the surface area. Topical BAC-3 was applied twice daily starting on the first day until the animals were sacrificed at day 45. Treatment groups included BAC-3 in a eucerin vehicle. Two concentrations of BAC-3 were used, 1% and 0.1%. Control treatments consisted of vehicle alone. There were no significant differences in body weights among the treatment groups during the 45 days of the study. Wound healing was assessed in vivo by measuring the distance across wound edges at days 14, 21, 28, 35 and 45. There were 6 rats per group. As shown in the figure, burn wounds decreased in size significantly faster in rats administered the 0.1% BAC-3 as compared with burn wounds on rats receiving vehicle alone. The rate of wound closures as assessed by calculating the linear regression coefficient.

Extent of burn wound closure with BAC-3 without chlorhexide (FIG. 2). Burns were induced on the dorsal surface of rats using standardized methods as described previously. The total burn area was equivalent to 7% of the surface area. Topical BAC-3 was applied twice daily starting on the first day until the animals were sacrificed on day 45. Treatment groups included BAC-3 in a eucerin vehicle. Two concentrations of BAC-3 were used; 1% and 0.1%. Control treatments consisted of vehicle alone. There were no significant differences in body weights among the treatment groups during the 45 days of the study. Wound healing was assessed in vivo by measuring the distance across wound edges at days 14, 21, 28, 35 and 45. There were 6 rats per group. As shown in the figure, burn wounds were significantly smaller in rats administered the 0.1% BAC-3 at days 14, 21 and 28 as compared with burn wounds in rats receiving the vehicle alone ($p<0.05$ by ANOVA). Mean values for each time point are shown as indicated by designated symbols; T-bars=2 SD. Significant differences ($p<0.05$ by ANOVA, with post hoc analysis using Fisher's PSLD) are indicated by an asterisk.

During the healing period, the hair growth of dead skin was very prominent in all rats of group 1-A. (1% BAC-3 in ointment), compared to the other groups where growth hair was just noticed.

B. Burning 15% of the Body Surface (10×5 cm)

Four rats were burned according to the described procedure using the wider opening in the Walker device (10×5 cm). All rats were treated from the beginning by placebo. After 50 days all burned rats had open wounds in average 2.3 cm at the neck, 1.3 cm in the middle and 1.8 cm at the tail.

On the $50^{th}$ day after burning, animals were treated with 1% BAC-3 in ointment without chlorhexidine hydrochloride using the following procedure:

For the first 3 days, burn wounds were treated twice daily. After developing granulation tissue and the first sign of epithelization, animals were treated 3 days with 1% BAC-3 in ointment once daily. For the next four days, animals were treated every second day. After that wounds were treated every third day with 1% BAC-3 in ointment until the entire wound was re-epithelized. Re-epithelization was first completed at the middle of the wounds, then at the tails and finally at the necks. Whole epithelization in all animals was finished in 30 days.

Incision Wounds

Figure 3:
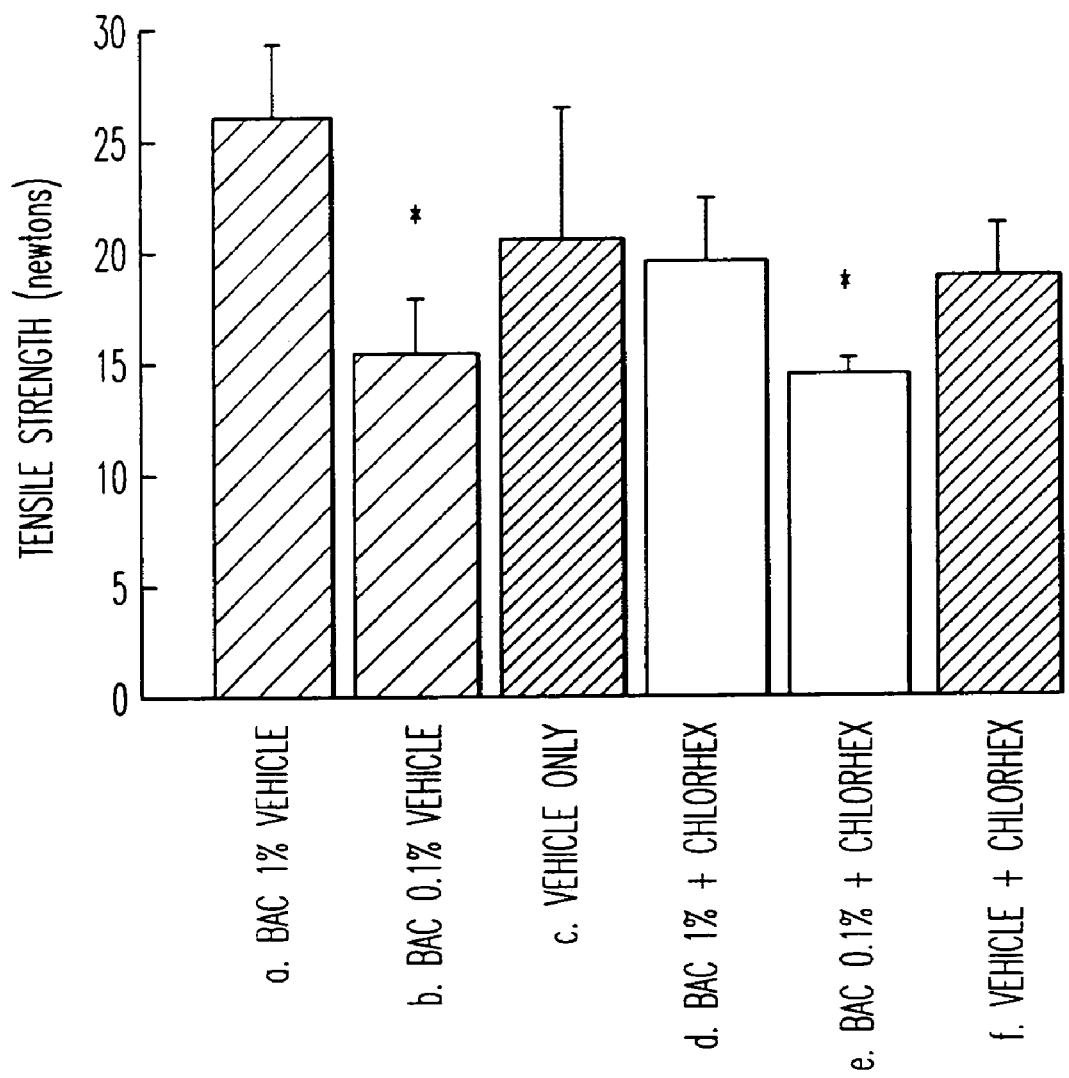
FIG. 3 provides a graphical representation of the effect of BAC-3 on the tensile strength of incision wounds.

Effect of BAC-3 on Tensile Strength of Incision Wounds (FIG. 3) with and without chlorhexidine hydrochloride. The tensile strength of incision wounds was measured 21 days after wounding. Rats were treated with preparations of BAC-3 as described above. Controls consisted of vehicle alone. As shown in FIG. 3, the tensile strength was significantly lower in wounds treated with 0.1% BAC-3 as compared with wounds treated with the corresponding vehicle ($p<0.05$ by ANOVA). This observed decrease in tensile strength is consistent with other known properties of BAC-3, particularly its ability to decrease the fibrotic response in wound healing. The most likely mechanism for the alteration in material properties of the granulation tissue is a decrease in production of the trifunctional collagen crosslink hydroxypyridinium and/or its dihydroxylated precursors. Increased levels of hydroxypyridinium are associated with increased tensile strength, increased stiffness, decreased solubility, and increased resistance to enzymatic digestion of the matrix. Abnormal production of hydroxypyridinium is specifically associated with hypertrophic scarring and keloid formation. It is likely that BAC-3 exerts its modulating effect on hydroxypyridinium formation by down regulating lysine hydroxylation, which in turn could be modulated either directly by the drug, or indirectly through known effects of BAC-3 on specific cytokines.

The prevention and treatment of burn shock, atherosclerosis and transplanted organ rejection and the treatment of depression or schizophrenia can be tested using the following procedures:

Provocation and Treatment of Burn Shock

The quality of a model for infliction of standard burns depends on its reproducibility. The consecutive burn wounds should ideally be identical in depth and extent.

For this purpose a standardization of the method practiced is imperative. This can be achieved by exactly defining the size and location of the burn wound, the temperature gradient, duration of exposure and method of applying the burn.

The standard animal burn are performed by techniques and device described by Walker. The device has an aperture that enables exposure of between 35-50% of the total rat skin surface. The surface of the skin is measured for every animal using Mech's formula: $A=kW^{2/3}$; A=surface area in $cm^2$; W=body weight in gm, k=10.

Method of burning. Each animal is anesthetized with pentobarbital administered i/p (5 mg/25 g). The hair over the dorsum is clipped with an Oster animal clipper, using a No. 40 blade. The animal is then placed supine in the burning device and the extremities tied. The malleable retractor is placed over the animal and secured snugly with plastic straps. The ensure device is then picked up by the retractor ends with forceps and the exposed area immersed in boiling water. Ten seconds of exposure is sufficient to produce a full-thickness burn. On removal from the water, the dorsum and flanks are gently dried by rolling on a towel and the animal released and individually caged. This procedure produces a uniform burn with sharp margins.

Procedure

In a different animal group of 6 Sprague-Dawley rats, the upper bracket surface is determined in which all burned animals die in 24 hours. This upper bracket surface is used as a surface needed for testing BAC-3 in prevention of burn shock.

Animal Model for Depression

It has been recently reported that Wistar Kyoto (WKY) rats manifest several behaviors that are suggestive of depression. WKY rats demonstrate immobility in the forced swim test. The fact that WKY rats are susceptible to restraint-induced stress ulcer and also reveal significantly higher levels of adrenocorticotropin hormone in response to restraint stress suggests that WKY rats are hyper-responsive to stress stimulation. The antidepressant desipramine, reduces immobility in the forced swim test and also reduces the incidence of stress ulcer in WKY rats.

Method and Procedure

The study uses 24 Wistar rats (WKY male rats). The WKY rats are provided by Taconic Farms (Germantown, N.Y.) from their line of WKY rats. Rats are housed with ad lib food and water and daylight conditions maintained between 0600 and 1800 h. Rats are 85-95 days old at the beginning of the study. The forced swim apparatus is a simple glass water tank which is 30 cm in diameter and 45 cm tall. The water level is 15 cm from the top. Water temperature is maintained at 25° C. Animals remain in the water for 15 min, during which time their behaviors are recorded. The rats are subsequently removed and allowed to dry for 15 min in a heated enclosure (32° C.), then returned to their home cages. This treatment produces long periods of immobility in the water (10-12 min total duration) and the rats on removal are mildly hypothermic (−3° C.) and are hypoactive for periods up to 30 min. The 24 rats are divided in 4 groups each of 6 rats. The first group receives an I.P. injection of BAC-3 10 mg/kg 24 hours and 1 hour before testing. The second group receives BAC-3 orally (10 mg/kg) 24 hours and 1 hour before testing. The third group receives only 0.9% NaCl I.P. The fourth group receives 0.9% NaCl orally. BAC-3 is dissolved in 0.9% NaCl and injected in a constant volume of 5 ml/kg.

Rats are individually placed in the water tank and their behavior is recorded. This includes the amount of time spent floating, the number of headshakes, and the number of bobbings. These behaviors are defined as follows: headshakes-shaking head and breaking water surface; bobbing-paddling with forepaws, and/or rear paws with head moving above and below water surface; floating-motionless without moving front or rear paws.

Differences from control values are assessed for statistical significance using Dunnett's test and Student's t test.

Animal Model for Schizophrenia

When mice are subjected to a weak stress, forced swimming for 3 min, and then treated repeatedly with phencyclidine (PCP) and subjected to the same stress again, the forced swimming-induced immobility was enhanced. The enhancing effect of PCP (10 mg/kg per day S.C.) on the immobility persisted for at least 21 days after withdrawal of the drug. PCP treatment could be consistent with the phenomena observed in schizophrenia and with the previous experimental reports, suggesting that the treatment could serve as an animal model for the negative symptoms of PCP psychosis. Although classical antipsychotics improve the positive symptoms of schizophrenia, they do not improve the negative symptoms. A recent advance in this field is the clinical introduction of compounds that have both dopamine-$D_2$ and 5-$HT_{2A}$ receptor antagonist properties, such as clozapine. Such compounds are thought to be efficacious in treating the negative symptoms of chronic schizophrenia. In the study, ritanserin, risperidone, and clozapine, at doses that failed to produce antidepressant effects in the control animals, attenuated the PCP-induced enhancement of immobility in the forced swimming test in mice. Thus it would appear that the behavioral change induced by repeated PCP treatment is a useful model for the negative symptoms of schizophrenia, since the ameliorating effects of these antipsychotics in this model would reflect their clinical effectiveness.

Mice of the C 57/black strain weighing 25-27 g at the beginning of the experiments are used. The animals are housed in plastic cages and are kept in a regulated environment (23+/−1 of, 50+/−5% humidity), with a 12 h/12 h light dark cycle. Food and tap water ad libitum. Mice are tested in forced swimming test.

First Measurement of Immobility

On the 1st day, each mouse is individually placed in a transparent glass cylinder (20 cm high, 8 cm in diameter), which contains water to a depth of 8 cm, and are forced to swim for 3 min. The duration of immobility (immobility time) is measured (first measurement of immobility) with a digital counter. The mice are matched according to the results of immobility time in the first measurement of immobility, and are divided into various treatment groups.

Drug treatment. On the 2nd day, drug treatment is started. Saline, PCP which produces negative symptom in humans, and BAC-3 (10 mg/kg I.P.) are administered once a day for 13 days. On the 15th day, saline treated animals are challenged with saline (control group), with PCP (10 mg/kg S.C. single PCP-treated group) and with BAC-3 (10 mg/kg I.P. repeated BAC-3 group) respectively. Other animals receive saline for 9 days, and are then treated with PCP (10 mg/kg S.C.) for 4 days. On the 15th day, such mice are challenged with PCP (10 mg/kg S.C.) and with BAC-3 (10 mg/kg I.P.).

Second Measurement of Immobility

On the 16th day, each mouse is placed in water again for 3 min, and the immobility time is recorded. BAC-3 is administered I.P. 1 h before the second measurement of immobility. Control mice receive vehicle only and the same procedure is performed.

Statistical Analysis

Statistical differences among values for individual groups is determined with Dunnett's multiple comparison test and Students t test.

Animal Model for Atherosclerosis (Cardiovascular Diseases)

Chylomicron remnants and intermediate density lipoprotein particles are highly atherogenic particles that are typically cleared rapidly from the blood by the interaction of apoE and either the LDL receptor of the LDL receptor-like protein primarily by the liver. In humans with genetic variation in the apoE gene or apoE deficiency this process is impaired and these particles accumulate in the plasma leading to premature atherosclerosis. In apoE-deficient mice a simian phenomenon is observed. ApoE-deficient mice have high plasma levels of these lipoprotein remnants. On a low-fat, low cholesterol diet levels of VLDL exceed 500 mg/DL. These mice develop widespread atherosclerosis. Extensive pathological studies have demonstrated that the quality of these lesions is similar to that of humans. They start as early subintimal foam cell deposits and progress to advanced fibroproliferative atherosclerotic lesions that contain substantial myointimal hyperplasia and extracellular matrix, hallmarks of human atherosclerosis.

Prevention of Organ Transplant Rejections

The use of rhamnolipid(s) in the prevention of organ transplant rejection is performed either in the model of murine pancreatic islets; or allogeneic bone marrow in graft-versus post-reactive and graft-versus-host-nonreactive situations in rat and/or a mouse model; or in a rat model of hind limb allotransplantation. In all models three groups are studied: unheated graft; grafts receiving 10-30 mg/kg/day of rhamnolipid started on post operative day 7 and rhamnolipid started on day 9 (10 mg/kg/day). At least one of the above mentioned conditions is used as a model in the prevention of transplant organ rejection.

This application is based on U.S. provisional application Ser. No. 60/075,959, filed in the U.S. Patent Office on Feb. 24, 1998, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

The invention claimed is:

1. A cosmetic method for the treatment of wrinkles comprising:
applying to a person having wrinkles, an effective amount of a composition comprising as an active ingredient, one or more rhamnolipids of Formula I:

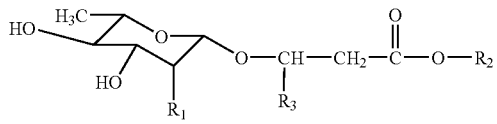

wherein $R^1$=H, unsubstituted α-L-rhamnopyranosyl, α.-L-rhamnopyranosyl substituted at the 2 position with a group of formula —O—C (=O)—CH=CH—$R_5$, or —O—C (=O)—CH=CH—$R_5$;
$R^2$=H, lower alkyl, —$CHR_4$—$CH_2$—COOH or —$CHR_4$—$CH_2$—$COOR_6$;
$R^3$=—$(CH_2)_x$—$CH_3$, wherein x=4-19;
$R^4$=—$(CH_2)_y$—$CH_3$, wherein y=1-19;
$R^5$=$(CH_2)_z$—$CH_3$, wherein z=1-12; and
$R^6$=lower alkyl.

2. The cosmetic method as claimed in claim 1, wherein said rhamnolipid of Formula 1 is α-L-rhamnopyranosyl-(1, 2)-α-L-rhamnopyranosyl)-3-hydroxydecanoyl-3-hydroxydecanoic acid having the following formula:

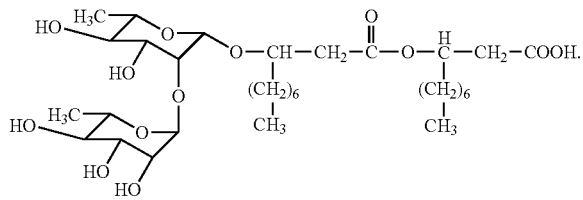

3. The cosmetic method as claimed in claim 1, wherein the one or more rhamnolipids of Formula 1 are selected from the group consisting of compounds of Formula 1 wherein:

$R^1$=—O—C(=O)—CH=CH—$R_5$, $R^2$=—$CHR_4$—$CH_2$—COOH, $R^3$=—$(CH_2)_6$—$CH_3$, $R^4$=—$(CH_2)_2$—$CH_3$, and $R^5$=—$(CH_2)_6$—$CH_3$;

$R^1$=α-L-rhamnopyranosyl substituted at the 2-position by —O—C(=O)—CH=CH—$R^5$, $R^2$=—$CHR^4$—$CH_2$—$COOCH_3$, $R^3$=$(CH_2)_6$—$CH_3$, $R^4$=—$(CH_2)_6$—$CH_3$, and $R^5$=—$(CH_2)_6$—$CH_3$;

$R^1$=—O—C(=O)—CH=CH—$R_5$, $R^2$=—$CHR_4$—$CH_2$—$COOCH_3$, $R^3$=—$(CH_2)_6$—$CH_3$, $R^4$=—$(CH_2)_2$—$CH_3$, and $R^5$=—$(CH_2)_6$—$CH_3$; and $R^1$=α-L-rhamnopyranosyl substituted at the 2-position by —O—C(=O)—CH=CH—$R^5$, $R^2$=—$CHR^4$—$CH_2$—$COOCH_3$, $R^3$=—$(CH_2)_6$—$CH_3$, $R^4$=—$(CH_2)_6$—$CH_3$, and $R^5$=—$(CH_2)_6$—$CH_3$.

4. A cosmetic method for the treatment of wrinkles comprising:
applying to a person having wrinkles, an effective amount of a composition comprising as an active ingredient, one or more rhamnolipids of Formula I:

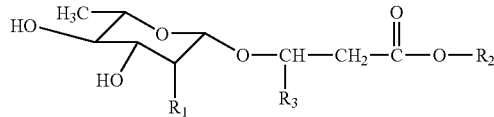

wherein $R^1$=H, unsubstituted a-L-rhamnopyranosyl, α.-L-rhamnopyranosyl substituted at the 2 position with a group of formula —O—C (=O)—CH=CH—$R_5$, or —O—C (=O)—CH=CH—$R_5$;
$R^2$=H, lower alkyl, —$CHR_4$—$CH_2$—COOH or —$CHR_4$—$CH_2$—$COOR_6$;
$R^3$=—$(CH_2)_x$—$CH_3$, wherein x=4-19;
$R^4$=—$(CH_2)_y$—$CH_3$, wherein y=1-19;
$R^5$=$(CH_2)_z$—$CH_3$, wherein z=1-12; and
$R^6$=lower alkyl;
wherein the composition is applied from 1-3 times per day to the wrinkled areas.

5. The cosmetic method as claimed in claim 1, wherein the composition is administered in topical form.

6. The cosmetic method as claimed in claim 1, wherein the composition further comprises one or more cosmetic carriers and/or diluents.

7. The cosmetic method as claimed in claim 1, wherein the rhamnolipid is administered in an amount averaging from about 0.01 to about 1.0% weight over a period of at least one day to six weeks.

* * * * *